US006867033B1

(12) United States Patent
Frazer et al.

(10) Patent No.: US 6,867,033 B1
(45) Date of Patent: Mar. 15, 2005

(54) TREATMENT OF PAPILLOMAVIRUS INFECTIONS

(75) Inventors: Ian Frazer, Buranda (AU); Jian Zhou, deceased, late of Jindalee (AU); by Xiao Yi Sun, legal representative, Jindalee (AU)

(73) Assignee: The University of Queensland of St. Lucia, Queensland (AU)

( * ) Notice: Subject to any disclaimer, the term of this patent is extended or adjusted under 35 U.S.C. 154(b) by 0 days.

(21) Appl. No.: 09/868,009

(22) PCT Filed: Dec. 13, 1999

(86) PCT No.: PCT/AU99/01108

§ 371 (c)(1),
(2), (4) Date: Nov. 21, 2002

(87) PCT Pub. No.: WO00/35478

PCT Pub. Date: Jun. 22, 2000

(30) Foreign Application Priority Data

Dec. 11, 1998 (AU) .............................................. PP7653

(51) Int. Cl.[7] ............................ C12N 7/00; C12P 21/06
(52) U.S. Cl. ................. 435/235.1; 435/69.1; 424/204.1
(58) Field of Search ........................... 435/320.1, 235.1, 435/69.1; 424/204.1; 530/300

(56) References Cited

U.S. PATENT DOCUMENTS

| 5,437,951 | A | | 8/1995 | Lowy et al. ................. 435/69.1 |
| 5,716,620 | A | | 2/1998 | Lowy et al. ............... 424/186.1 |
| 5,744,142 | A | | 4/1998 | Lowy et al. ............... 424/204.1 |
| 5,821,087 | A | | 10/1998 | Lowe et al. ................. 435/69.3 |
| 5,888,516 | A | * | 3/1999 | Jansen et al. ............. 424/204.1 |
| 6,436,402 | B1 | * | 8/2002 | Zhao et al. ............... 424/189.1 |

FOREIGN PATENT DOCUMENTS

| WO | WO 93/02184 | 2/1993 |
| WO | WO 96/15247 | 5/1996 |
| WO | WO 96/29413 | 9/1996 |
| WO | WO 96/30520 | 10/1996 |
| WO | WO 98/10790 | 3/1998 |
| WO | WO 98/15631 | 4/1998 |
| WO | WO 98/28003 | 7/1998 |
| WO | WO 98/44944 | 10/1998 |
| WO | WO 99/09177 | 2/1999 |
| WO | WO 99/18220 | 4/1999 |
| WO | WO 00/35478 | 6/2000 |

OTHER PUBLICATIONS

Stanley M. A. , Expert Rev. Vaccine, Jun. 2003; 2(3):381–389.*
Frazer I. , Virus Research, 2002; 89: 271–274.*
Peng et al , Pathology, 1999, vol. 31, pp. 418–422.*
Barrasso, "Treatment of genital warts: an Overview", *J. Obstet. Gynecol.* 18:S70–1(1998).
Bavinck, "HPV Infections and Immunosuppression", *Clin. Dermatol.* 15:427–37(1997).
Bernard, "Evolution of Papillomaviruses", *Curr. Topics Microbiol. Immunol.* 186:34–51(1994).
Beutner, "Therapeutic approaches to Genital Warts", *Am. J. Med.* 102:28–37(1997).
Beutner, "Imiquimod, a Patient–Applied Immune–Response Modifier for Treatment of External Genital Warts", *Antimicrobial Agents and Chemotherapy*, 42:789–794(1998).
Breitburd, "Immunization with Viruslike Particles from Cottontail Rabbit Papillomavirus (CRPV) Can Protect against Experimental CRPV Infection", *J. Virol.* 69:3959–3963(1995).
Broker, "Structure and Genetic Expression of Papillomaviruses", *Obtsect. Gynecol Clin. N. Am.* 14:329–43(1987).
Carter, "The Natural History of Human Papillomavirus Type 16 Capsid Antibodies among a Cohort of University Women", *Infec. Dis.*, 174:927–36 (1996).
Coleman, "Immunological Events in Regressing Genital Warts", *Anat. Pathol.*, 102:768–73(1994).
Christensen, "Human Papillomaviruses Types 6 and 11 Have Antigenically Distint Strongly Immunogenic Conformationally Dependent Neutralizing Epitopes", *Virol.*, 205, 329–35(1994).
Christensen, "Immunization with Viruslike Particles Induces Long–Term Protection of Rabbits against Challenge with Cottontail Rabbit Papillomavirus", *J. Virol.* 70:960–65(1996).
De Bruijn, "L1 Specific Protection from Tumor Challenge Elicited by HPV16 Virus–like Particles", *Virol.* 250:371–6(1998).
Dupuy, "Cell mediated immunity induced in mice by HPV16 L1 virus–like particles", *Microbial Pathogenesis* 22:219–25(1997).
Evander, "Identification of the $\alpha_6$ Integrin as a Canditate Receptor for Papillomavirus", *J. Virol.* 71:2449–56(1997).
Frazer, "Immunology of Papillomavirus infection", *Curr. Opin. Immunol.* 8:484–91(19960.
Giri, "Papillomavirus genomes: from sequence data to biological properties", *TIG* 2:227–32(1986).

(List continued on next page.)

Primary Examiner—Ali R. Salimi
(74) Attorney, Agent, or Firm—Beth A. Burrous; Foley & Lardner LLP

(57) ABSTRACT

This invention relates to treatment of papillomavirus infections. Primarily there is provided a method of treatment of an existing papillomavirus (PV) infection which includes the step of administration of PV VLPs selected from the group consisting of PV L1 VLPs and PV L1/L2 VLPs to a patient suffering from the PV infection. Suitably the PV infection is characterised by the presence of epithelial lesions. The major infection which is treated are gential warts caused by HPV 6 and HPV 11.

11 Claims, 8 Drawing Sheets

OTHER PUBLICATIONS

Figure 1A:

Greenstone, "Chimeric papillomavirus virus–like particles elicit antitumor immunity against the E7 oncoprotein in a HPV16 tumor model", *Proc. Natl. Acad. Sci. USA* 95:1800–5(1998).

Hagenese, "Progress in the Development of HPV Vaccines", *Infect. Med.* 14:555–64(1997).

Hines, "Prospects for Human Papillomavirus vaccine development: emerging HPV vaccines", *Curr. Opin. Inf. Dis.* 11:57–61(1998).

Kirnbauer, "Efficient Self–Assembly of Human Papillomavirus Type 16 L1 and L1–L2 into Virus–like Particles", *J. Virol.* 67:6929–36(1993).

Kirnbauer, "Papillomavirus L1 major capsid protein self–assembles into virus–like particles that are highly immunogenic", *Proc. Natl. Acad. Sci. USA* 89:12180–4(1992).

Kirnbauer, "Virus–like Particles of Bovine Papillomavirus Type 4 in Prophylactic and Therapeutic Immunization", *Virol.* 219:37–44(1996).

Park, "Human papillomavirus type 16 E6, E7 and L1 and type 18 proteins produced by recombinant baculovirus", *J. Virol. Meth.* 45:303–18(1993).

Peng, Papillomavirus Virus–like Particles Can Deliver Defined CTL Epitopes to the MHC Class 1 Pathway, *Virol.* 240:147–57(1998).

Price, "$\alpha_6$ Integrins Are Required for Langerhams Cell Migration from the Epidermis", *J. Exp. Med.* 186:1725–35(1997).

Qi, "Epithelial Cells Display Separate Receptors for Papillomavirus VLPs and for Soluble L1 Capsid Protein", *Virol.* 216:35–45(1996).

Rose, "Expression of Human Papillomavirus Type 1 1 L1 Protein in Insect Cells: In Vivo and In Vitro Assembly of Viruslike Particles", *J. Virol.* 67:1936–44(1993).

Rose, "Serological differentiation of human papillomavirus types 11, 16 and 18 using recombinant virus–like particles", *J. Gen. Virol.* 75:2445–9(1994).

Sasagawa, "Synthesis and Assembly of Virus–like Particles of Human Papillomavirus Type 6 and Type 16 in Fission Yeast Schizosaccharomyces pombe", *Virol.* 206:126–35(1995).

Salzman et al. "Sequence Analysis of Papillomavirus Genomes" in "The Papovaviridiae: vol. 2, the Papillomavirus" Plenum Press (1987).

Schiller, Papillomavirus–Like Particles, *Papillomavirus Report*, 6:121–8(1995).

Schirmbeck, "Virus–like Particles Induce MHC Class I–Restricted T Cell Responses", *Intervirol.* 39:111–9(1996).

Sing, "Isolation of Epstein–Barr Virus (EBV)–Specific Cytotoxic T Lymphocytes That Lyse Reed–Sternberg Cells: Implications for Immune–Mediated Therapy of EBV[+] Hodgkin's Disease" *Blood* 89:1978–86(1997).

Sokolowski, "mRNA Instability Elements in the Human Papillomavirus Type 16 L2 Coding Region", *J. Virol.* 72:1504–15(1998).

Stuart–Harris, "Clinical Applications of the Interferons", *Chapman and Hall Medical*(1997).

Suzich, "Systemic immunization with papillomavirus L1 protein completely prevents the development of viral mucosal papillomas", *Proc. Nat. Acad. Sci. USA* 92:11553–7(1995).

Walter, "Reconstruction of Cellular Immunity Against Cytomegalovirus in Recipients of Allogeneic Bone Marrow by Transfer of T–Cell Clones from the Donor", *New England J. Med.* 333:1038–44(1995).

Yamada, "Human Papillomavirus Type 16 Variant Lineages in United States Populations Characterized by Nucleotide Sequence Analysis of the E6, L2 and L1 Coding Segments", *J. Virol.* 69:7743–53(1995).

Zhou, "Expression of Vaccinia Recombinant HPV 16 L1 and L2 ORF Proteins in Epithelial Cells Is Sufficient for Assembly of HPV Virion–like Particles", *Virol.* 251–7(1991).

* cited by examiner

TREATMENT OF PAPILLOMAVIRUS INFECTIONS

CROSS-REFERENCE TO RELATED APPLICATIONS

The present application is a National Stage of International Application No. PCT/AU99/01108, filed Dec. 13, 1999, which claims priority to Australian Patent Application No. PP 7653, filed Dec. 11, 1998.

FIELD OF THE INVENTION

THIS INVENTION relates to treatment of papillomavirus infections.

BACKGROUND OF THE INVENTION

Infection of the anogenital skin with human papillomavirus (HPV) results in exophytic or flat warts, and infection with some genotypes is also accepted as an antecedent cause of anogenital cancer. Current treatment modalities for genital warts are generally destructive and include surgery, cautery, laser surgery, and caustic chemicals as described in, for example, Beutner et al., 1997, Am. J. Med. 102 28–37. There is a high treatment failure and disease relapse rate, varying from 30–70%, after destructive treatment of exophytic warts which is discussed in Barrasso, R., 1998, J. Obstet. Gynecol. 18 S70–S71. Warts persist longer and return more frequently in immunosuppressed patients as referred to in Bouwes et al., 1997, Clin. Dermatol. 15 427–437, suggesting a role for the immune system in the resolution of the lesions. A role for local immunity is further supported by the partial therapeutic effectiveness of interferons as referred to in Frazer, I. H. & McMillan, N. A. in Clinical Applications of the Interferons (eds. Stuart-Harris, R. & Penny, R. W.) 79–91 (Chapman and Hall Medical, London, 1997), and of topical application of the immune enhancer Imiquimod which is discussed in Beutner et al., 1998, Antimicrob. Agents Chemother. 42 789–794. Immunoprophylaxis against HPV infection is proposed which is discussed in Hines et al., 1998, Curr. Opin. Infect. Dis. 11 57–61 and Hagensee, M. E., 1997, Infect. Med. 14 555–556, particularly because of the association of some papillomavirus (PV) genotypes with cancer. Expression of the PV capsid protein L1 or the L1 and L2 proteins in eukaryotic expression systems results in the assembly of this protein into papillomavirus virus-like particles (VLPs) described in Zhou et al., 1991, Virology 185 251–257; Kirnbauer et al., 1992, Proc. Natl. Acad. Sci. USA 89 12180–12184 and Rose et al., 1993, J. Virol. 67 1936–1944, which morphologically and immunologically resemble the native virus. Immunization with recombinant VLPs of the relevant type results in effective prophylaxis against challenge with bovine, canine and cottontail rabbit papillomavirus in vivo as referred to in Breitburd et al., 1995, J. Virol. 69 3959–3963, Kirnbauer et al., 1996, Virology 219 37–44 and Suzich et al., 1995, Proc. Natl. Acad. Sci. USA 92 11553–11557, and protection correlates with antibody titre and can be transferred with antibody (Brietburd et al, 1995, supra).

Reference may also be made to U.S. Pat. No. 5,437,951 which makes it clear that it is already known that the ability of PV VLPs to induce high titre neutralizing antiserum makes them suitable for prophylaxis against communicable papillomatosis. Examples of appropriate subjects provided in this reference are (i) bovine animals which are susceptible to papilloma warts, (ii) all humans for non-genital types of HPV infection and (iii) sexually active humans for genital types of HPV infection.

U.S. Pat. No. 5,437,951 also makes it clear that prophylactic vaccination can be useful for productive PV lesions which usually express L1 and L2 capsid proteins. Such lesions may occur in benign infections such as warts of laryngeal papillomatosis. This reference also establishes that protective immunity against both benign and malignant PV disease can be induced by administration of an effective amount of recombinant L1 capsid protein to an individual at risk for PV infections. A vaccine comprising the capsid protein can be directly administered either parentally or locally according to conventional immunization protocols.

Thus, U.S. Pat. No. 5,437,951 as well as the Kirnbauer et al., 1996, supra, Breitburd et al., 1995, supra and Suzich et al., 1995, supra references are representative of a large number of references that show that is well known that vaccines containing PV VLPs can be used for prophylaxis or prevention of infection of papilloma warts.

Reference may also be made to the Kirnbauer et al., 1996, supra wherein it was ascertained that immunization with vaccines containing BPV L1-L2 VLPs in Incomplete Freund's adjuvant to calves with established papillomas was not as efficient as the use of these vaccines for prophylaxis.

It is also noted in Greenstone et al., 1998, Proc. Natl. Acad. Sci. USA 95 1800–1805 that while PV VLPs are a promising prophylactic vaccine candidate to prevent HPV infections, they are unlikely to have therapeutic effects because the virion capsid proteins are not detected in the proliferating cells of infected epithelia or in cervical carcinomas. In this reference, it was also found that injection of chimeric HPV16L1/L2-HPV16 E7 VLPs into mice protected the mice from tumour challenge even in the absence of adjuvant. However, HPV16L1/L2 VLPs were not effective in this regard, a not unexpected result since the tumor was and E7 bearing tumor.

A similar result was found in Peng et al., 1998, Virology 240 140–157 wherein hybrid or chimeric VLPs formed from HPV L1 which also incorporated a single HPV16 E7 cytotoxic T lymphocyte (CTL) epitope and a single HIV gp 160 CTL epitope induced a strong CTL response upon immunization.

Reference may also be made to WO98/28003 which reports studies on development of a therapeutic vaccine to treat cotton tail rabbit papillomavirus infection. Their data supports the premise that E proteins are an essential component of an effective therapeutic vaccine.

This belief in the requirement for various E proteins to formulate a therapeutic PV vaccine has led to a clinical trial for a HPV6 genital wart therapeutic based on L2E7 absorbed onto Alhydrogel (Thomson et al., (1999) Phase 1 safety and antigenicity of TA-GW, a recombinant HPV5 L2E7 vaccine for the treatment of genital warts. Vaccine 17 40–49)

Interestingly, even though most vaccine trials have incorporated various adjuvants as a formulation component, their importance has not been determined. On this subject reference may be made to Shirmbeck et al., 1996, Intervirology 39 111–119 which also showed that injection of 100 ng to 1 $\mu$g of native hepatitis B virus surface antigen (HBsAg) VLPs without adjuvant efficiently primes MHC Class I restricted CTL responses and that this demonstrates that such VLPs may be immunogenic.

Unexpectedly, it has now been ascertained by the present inventors that treatment of existing PV infections, inclusive of genital warts, can be achieved by vaccines containing PV VLPs without any E proteins or adjuvant. This is doubly surprising especially in the light of the observations made in the Greenstone et al., 1998, supra and Kirnbauer et al., 1996, supra references above. The Kirnbauer et al., 1996, supra and Peng et al., 1998, supra also establish that while use of prophylactic PV vaccines without adjuvant may be effective, this conclusion may only apply to chimeric VLPs. While Schirmbeck et al., 1998, supra establishes that HBsAg VLPs without adjuvant may be immunogenic, a similar conclusion could not be applied to PV VLPs having regard to the other references described above.

SUMMARY OF THE INVENTION

It therefore is an object of the invention to provide a method of treatment of existing PV infections which is effective in use.

The invention, therefore, provides a method of treating an existing PV infection which includes the step of administration of PV VLPs selected from the group consisting of PV L1 VLPs and PV L1/L2 VLPs to a patient suffering from the PV infection.

However, the method of the invention is especially applicable to existing genital warts which are caused by HPV types 6, 11, 34, 39, 41–44 and 51–55. The warts that may be especially relevant for treatment are caused by HPV6 and HPV11.

Preferably the PV infections are epithelial lesions and more preferably such lesions are selected from the group consisting of palmar warts, planter warts, ano-genital warts, flat and planar warts of the skin and muscosal surfaces, CIN, equine sarcoid or replicating or vegetative PV infection.

Preferably in the course of treatment, an existing patient may be checked for the cause of his or her infection and, in this regard, a biopsy may be taken for PV typing. Suitably, the PV typing is effected by antibody-based or nucleic acid-based techniques which are well known to those skilled in the art. Preferably the PV-typing is effected by nucleic acid amplification techniques such as PCR.

The relevant VLPs may be produced by standard methods well known in the art which, for example, are reported in Qi et al., 1996, Virology 216 35–45. Such standard methods are also described in International Publication No. WO93/02184, Australian Pat. No. 683220, Yamada et al., December 1995, J. Virol. 7743–7753, U.S. Pat. No. 5,437,951, U.S. Pat. No. 5,744,142, Rose et al., 1993, supra, Kirnbauer et al., 1993, J. Virol. 67(12) 6929–6936, Sasegawa et al., 1995, Virology 206 126–135 and Schiller and Roden, 1995, Papillomavirus Report 6(5) 121–128.

The above disclosures are only referred to by way of example and make it clear that VLPs can be produced by a wide variety of methods which basically include cloning the L1 (or L1 and L2) gene into a suitable vector and expressing the corresponding conformational coding sequences for these proteins in a eukaryotic cell transformed by the vector. Subsequently all of the capsid protein coding sequence should be expressed and thus substantially all of the capsid coding sequence is cloned. Insect cells are preferred host cells although yeast cells may also be utilized if required.

Similarly, other eukaryotic and prokaryotic systems may be used to express L1 or L1 and L2 proteins provided the expressed proteins self-assemble into VLPS.

Preferably a baculovirus expression system is used wherein the L1 or L1 and L2 genes are inserted into a baculovirus expression vector containing flanking baculovirus sequences to form a gene construct and the recombinant DNA is co-transfected with wild-type baculovirus DNA into Sf-9 insect cells.

Reference is made to the Experimental Section hereinafter wherein human patients were treated with HPV6b VLPs without adjuvant. However, it is clear from International Publication No. WO93/02184 that the L1 ORF is monotonously conserved in all known cases and because of this, the invention has broad application to all PV types. Support for this conclusion may be demonstrated in the following references, i.e.:

(a) Carl C. Baker Appendix "Sequence Analysis of Papillomavirus Genomes" in "The Papovaviridiae: Volume 2, the Papillomaviruses", editors N. P. Salzman and P. M. Howley, Plenum Press (1987);

(b) Thomas R. Broker, 1987, "Structure and Genetic Analysis of Expression of Papillomaviruses", Obstetrics and Gynecology Clinics of North America 14(2) 329–348;

(c) Isabelle Giri and Olivier Danos, 1986, "Papillomavirus genomes: from sequence data to biological properties", 2 Trends Genet 2 227–232; and (d) A review by Syrjanen K. et al. in "Papillomaviruses and Human Disease", Springer Verlag, 1987.

It will be appreciated that the PV VLPs may be dissolved in any suitable physiological vehicle inclusive of saline, water, PBS (phosphate buffered saline). Suitable concentrations of PV VLPs are 0.5–20 µg and more preferably 1–10 µg. Dosages may be 3–6 times over a period of 8–16 weeks or more preferably 2–4 weeks.

In another aspect of the invention, and as demonstrated in the Experimental Section hereinafter, it is also evident that immunization with HPV6 and more particularly HPV6b VLPs give immune responses cross reactive with HPV11 but not HPV16. Therefore, immunization with HPV6 VLPS may provide protection against HPV11 infections and vice versa, i.e. immunization with HPV11 VLPs may give protection against HPV6 infections. In immunization protocols, similar concentrations or dosages of VLPs as described above may be adopted and use of any physiological vehicle may be utilized.

Any convenient route of administration may be adopted but parenteral administration and, in particular, intramuscular administration, is preferred.

EXPERIMENTAL

Materials and Methods

Patients

Consenting subjects (i.e. 36 in all) were recruited for the purpose of this clinical trial. Such subjects were healthy and had genital warts. They were also between the ages of 16 and 55 and with at least one visible external wart. The subjects had no treatment for their warts in the four weeks prior to immunization, and agreed to forego other treatments during the period of immunotherapy. Duration of genital wart disease, and prior treatment history, were recorded but were not used as a determinant of eligibility for participation, because of uncertainty amongst the patients as to how long the disease had been present and what the nature of prior topical treatments might have been. Patients were excluded if they had been treated for warts within the last four weeks, if they had a systematic illness undergoing medical management, if there were other active sexually transmitted infections in need of treatment, or if cervical dysplasia in need of treatment was detected on a PAP smear. Internal genital warts were not a contraindication to participation. A biopsy was taken of a representative wart at the time of recruitment, for HPV typing by PCR, and all warts were HPV6b/11 positive by PCR. HIV-1 testing was not routinely performed in this study, as only five cases of HIV infection had been detected in sentinel studies at the time of the study.

Average time between initial presentation with warts and first administration of vaccine to eligible patients was one week. Blood for HPV VLP antibody studies was also obtained from relevant laboratory staff, age matched with the patients, and without a history of genital warts.

Production of Vaccine Material

VLPs were produced under good laboratory practice conditions using an HPV6bL1 recombinant baculovirus (L1rBV) previously described in Qi et al., 1996, Virology 216 35–45. Cultures of SF9 cells in SF900-II medium (Sigma), were infected with L1rBV at an MOI of 10. After 48 hours, cultures were harvested, and the cell pellets pooled, assayed for L1 by immunoblot and for VLPs by electron microscopy, and frozen at −80° until further use. Thawed cell pellets were further purified by discontinuous sucrose gradient centrifugation, and by continuous Cesium Chloride gradient centrifugation, and assayed for VLP content, as previously described in Qi et al., 1996, supra and Park et al., 1993, J. Virol. Methods 45 303–318. Material of density 1.26–1.30 g/cm$^3$, which was >80% HPV6bL1 protein by gel analysis, and contained substantially complete virus particles on EM (VLPs), was then subjected to exhaustive dialysis against phosphate buffered 0.9% NaCl with Calcium and Magnesium(PBS), and aliquoted at 50 µg protein/100 µl in glass vials. A random sample of 10% of these vials were subjected to testing for sterility, pyrogenicity, and abnormal toxicity in rabbits. Material was sterile and negative for pyrogens, and no toxicity was observed. At the end of the study, one year after the pool of cell lysate was prepared, a vial was checked for VLP content by immunoblot and electron microscopy to confirm product stability.

Immunization

Subjects were examined every two weeks, and warts were inspected at each visit and generally photographed. Colposcopy with visualisation of the vagina and cervix was undertaken at each visit. At weeks 0, 4, and 8 patients were immunized with HPV VLPS, 1, 5 or 10 µg intramuscularly without adjuvant. Dose allocation was initially sequential, the first five patients receiving 1 µg, the next five 5 µg and the next five 10 µg. Thereafter, patients were allocated to receive 10, 5, or 1 µg alternately. If warts had not cleared by week 12, further VLP immunizations were offered at week 12, and if warts were not cleared, at week 16 and week 20. Four subjects (2×5 µg; 2×10 µg) received four immunizations, two subjects (1×5 µg; 1×10 µg) received five immunizations, and six patients (1×1 µg; 2×5 µg; 3×10 µg) received six immunizations. One patient who received 1 µg initially, and had failed to develop resolution or DTH to VLPs by week 10 with that dose, received three further vaccinations with 10 µg, and data for this patient were analysed with the 10 µg treatment group. Otherwise, supplementary immunizations where given were of the same dose of VLPs as initially given. Available subjects (n=34) were evaluated for outcome at week 20, and subjects were classified as evaluable if they received at least three immunizations and were seen at this time point.

Safety and Toxicity

A cohort of five patients receiving 10 µg VLPs were tested for routine haematology (FBE, Differential White Count), and biochemistry (AST, ALT, Bilirubin, Alkaline Phosphatase, Total Protein, Albumin, Globulins, Glucose, Urea, Creatinine, Uric Acid) tests prior to, and three days, 1, 2, 4, 8, and 12 weeks after the first immunization. Samples from subjects were tested by 12 channel automated chemistry analyzer (Beckmann CX4) and 6 channel Coulter haematology (Coulter T-540) analyzer.

All subjects were observed for adverse effects following each vaccination, and were asked at each visit about adverse events experienced between visits, including local discomfort at the site of the vaccination or of the warts, and systemic symptoms including fevers, chills, myalgia, headaches, and skin disorders.

Antibody to VLPs

Serum was collected prior to entry and every two weeks throughout the study, for assay for VLP specific antibody by ELISA. ELISA plates (Flow Laboratories) were coated with HPV6b, HPV11 or HPV16 VLPs (10 µg/ml) in PBS buffer, held overnight, and blocked with defatted skim milk. Test and control sera were added at 1:100 dilution and binding detected by HRP-conjugated anti-human IgG (Sigma) or HRP-conjugated anti-human IgG, A, M (Silenius). Mean reactivity of each serum with defatted skim milk, which ranged from 0.001 to 0.113 (mean 0.032) was in each case subtracted. For comparisons, the complete set of sera was tested within a single assay and three independent assays of the serum set were carried out with highly correlated results ($r^2 > 0.95$).

DTH Testing

VLP vaccine material was used as an antigen for DTH testing. DTH testing was carried out for 32 subjects after the primary three dose immunization and antibody testing protocol was complete at week 10–12. 20 µl (10 µg) of VLP suspension was delivered intradermally on the volar aspect of the forearm. Biopsies were scored visually at 48 hours as 0 (no induration), 1 (1–3 mm duration), 2 (4–10 mm induration) and 3 (>10 mm induration). For 28 subjects, DTH sites were biopsied using, a 3 mm punch biopsy under 1% Lignocaine local anaesthesia. Biopsies were fixed in neutral buffered formalin, and processed for routine H+E sections and for immunohistochemistry as previously described in Pettit et al., 1997, J. Immunol. 159 3681–3691.

Immunohistochemistry

Sections of biopsies fixed in neutral buffered formalin and routinely processed and embedded in paraffin, were de-paraffinized and subjected to high-temperature antigen retrieval (121° C., 10 minutes) using 10 mM EDTA, pH 7.5 buffer. Double immunostaining with combinations of CD1a/HLA-DR, CD1a/CD68, CD3/CD68, CD3/CD8, CD68/HLA-DR, CD3/HLA-DR and CD3/CD20 was carried out. Subsequent to blocking with 10% swine serum/10% FBS in TBS pH 7.6 for 1 hour, sections were incubated at room temperature in wet-chamber with primary antibodies; mouse anti-human CD1a (Immunotech-Coulter, clone BL-6 prediluted), rabbit anti-human CD3 (1:250) and mouse anti-human CD8 (clone C8/144B), CD68 (clone PG-M1), HLA-DR (clone TAL-1B5) and CD20 (clone L26) (DAKO, Denmark) all in 1:50 dilutions for 60 minutes. Sections were treated with biotinylated rabbit anti-mouse or swine anti-rabbit (1:200) secondary antibody and with streptavidin conjugated horseradish peroxidase (DAKO, Denmark) (1:300). For double immunostaining, the sections were further treated with second primary antibody followed by its corresponding biotinylated second secondary antibody. Streptavidin ABC/alkaline phosphatase conjugate (DAKO, Denmark) was used to tag the second antibody. The first and second antibodies were subsequently demonstrated by developing with substrate chromogen kits using DAB (brown) and Fast-red (red) (DAKO, Denmark). Sections were counterstained using Myer's haematoxylin.

Statistical Analysis

Univariate and multivariate analysis was carried out using Statistica Version 5.0 (Statsoft, Okla., U.S.A.).

Results

Vaccination and Adverse Reactions

As stated above, 36 subjects were recruited to the study, and 34 subjects were immunized with 1, 5 or 10 μg of HPV6bL1 VLPs on three or more occasions and also attended the week 20 evaluation (Table 1). The majority of subjects had had warts for two months or more (Table 2), and had at least one prior treatment with cautery for their warts. No local or lesional systemic adverse reactions were observed or reported by subjects (evaluable or otherwise) following immunization, beyond the immediate discomfort associated with injection. All of the biochemical and haematological analyses were within the local reference ranges at each visit, and there was no trend for change with time. Amongst those patients with regressing warts, no particular local reaction in the regressing warts was observed or reported, and warts appeared to regress without local inflammation in immunized subjects, as has generally been described for spontaneous regression of genital warts. Thirty-three subjects who were immunized on three or more occasions and who attended the 20 week follow up visit were regarded as evaluable for immune response to the vaccine and for outcome.

DTH to HPV6bL1 VLPs

Figure 1B:

VLP specific DTH was measured using a single intradermal injection of VLPs at various times after the second or third immunization. DTH was not tested prior to initiating immunization, primarily to avoid a immunising effect of the DTH skin test. The majority of patients, regardless of dose of VLPs or time after immunization, had a 2+ to 3+ clinical DTH response, and all patients had some visible response. For 28 subjects, DTH reactions were biopsied using a 3 mm skin punch, and subjected to histologic analysis including, for five biopsies, detailed immunohistochemical assessment. Typical DTH reaction including lymphoid and monocytic infiltrate was observed round vessels and subcutaneously (FIG. 1). Infiltrates for the five biopsies so assessed included CD1a+ve Langerhans cells, CD4 and CD8+ve T cells, and DR+ve macrophages. A five point scale was used for assessing DTH reactions histologically, according to the extent of the inflammatory infiltrate round blood vessels and subcutaneously, the number of involved vessels, and the presence of non-lymphoid inflammatory cells including eosinophils. The majority of the biopsies scored highly, and the DTH score was independent of VLP dose or number of immunizations.

In particular, CD1a+ Langerhans cells were seen in the epidermis, and rarely in the dermis, and some CD1a+ve cells co-expressed HLA-DR. The perivascular mononuclear inflammatory infiltrate was predominantly of CD3+ T-cells, with CD68+ macrophages and a few CD20+ B cells. Approximately 8–10% of the CD3+ T-cells were CD8+. Numerous HLA-DR+/CD3+ activated T-cells and some CD68+/DR+ macrophages were demonstrable in the dermis and in deeper tissue.

Antibody to VLPs

Figure 2A:
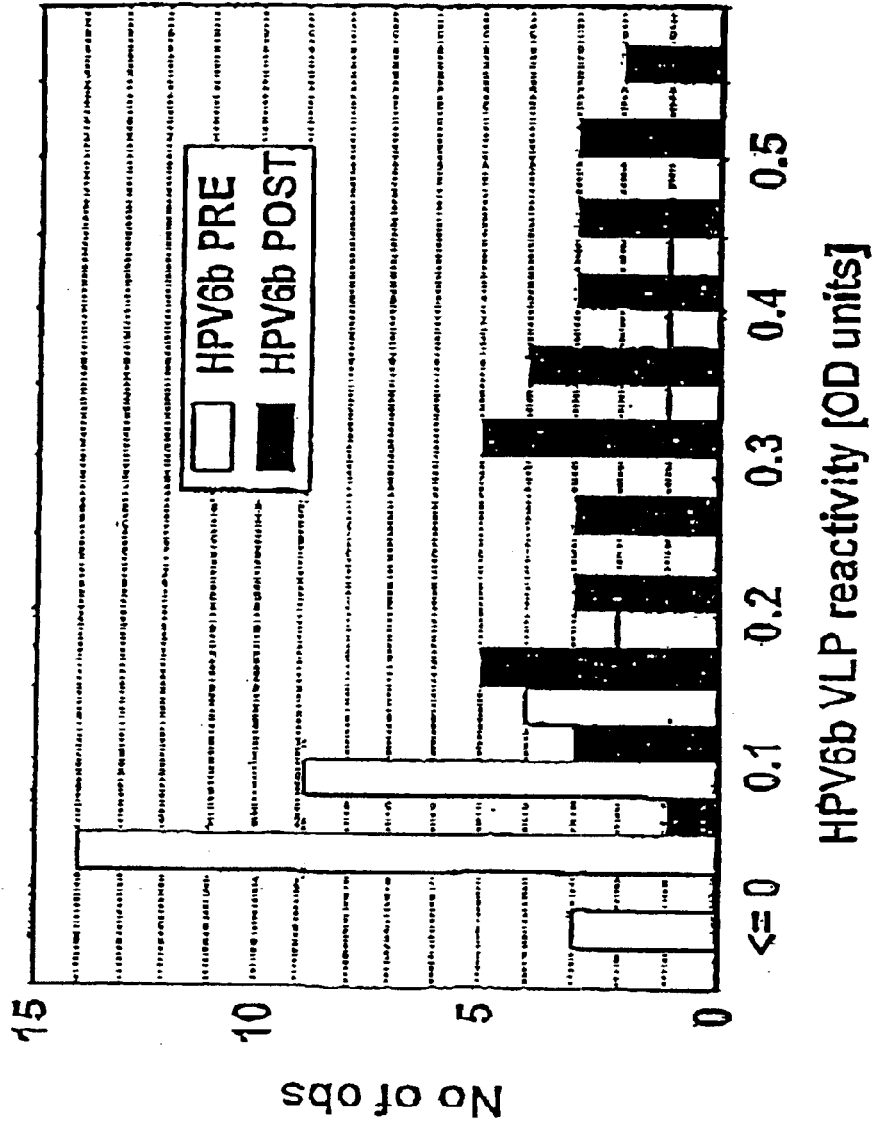
Figure 2B:
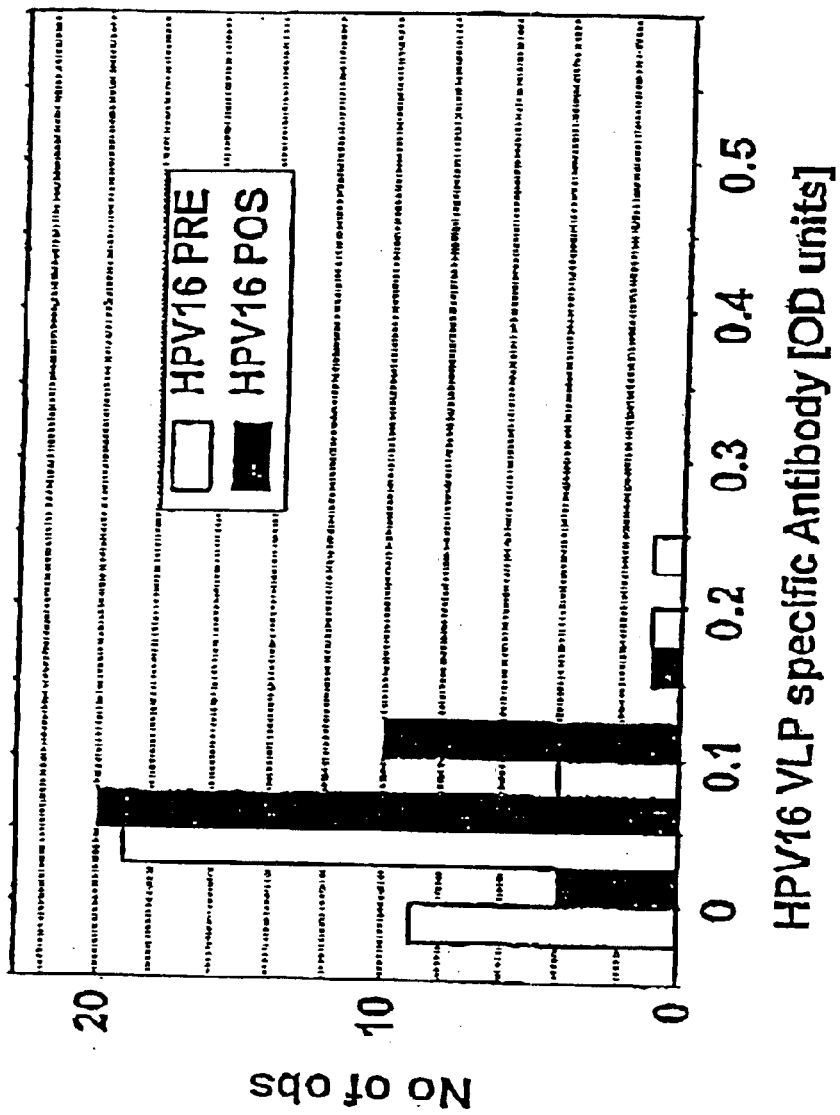
Figure 2C:
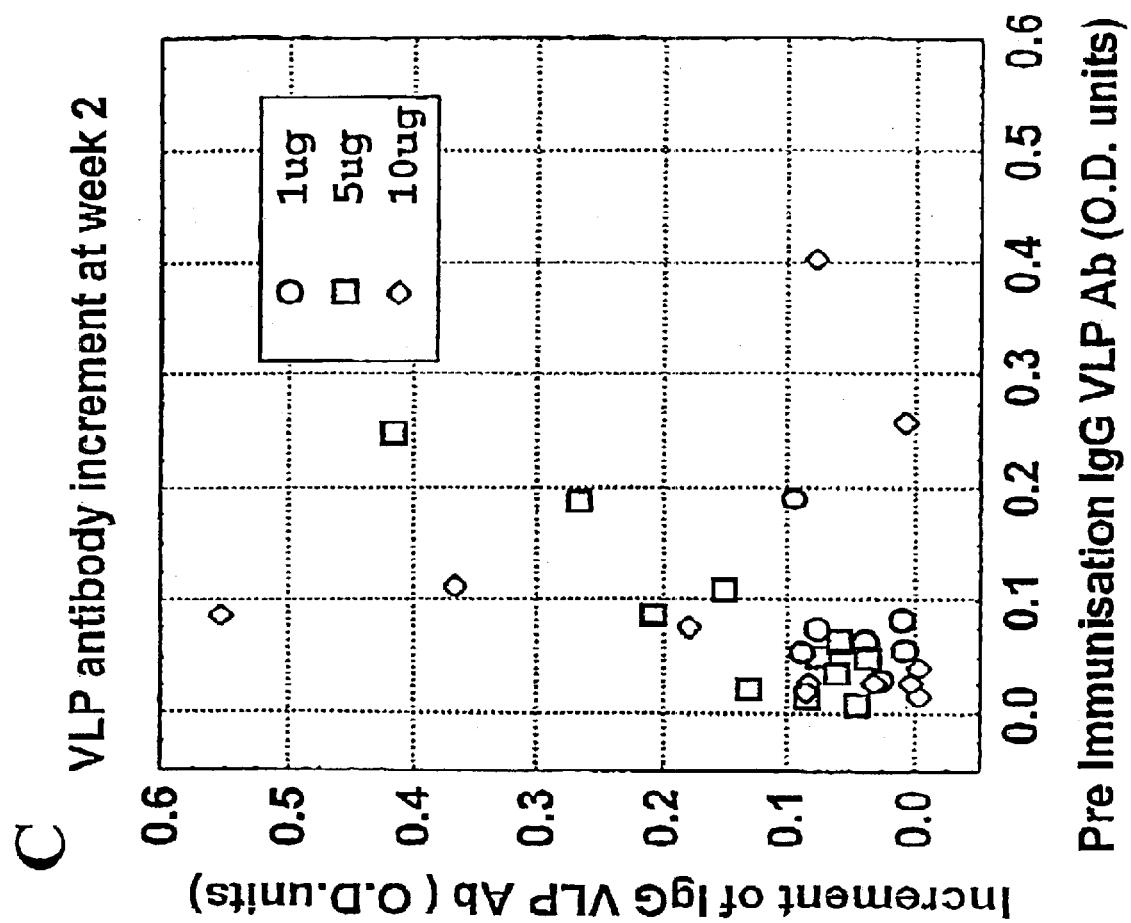
Figure 2D:
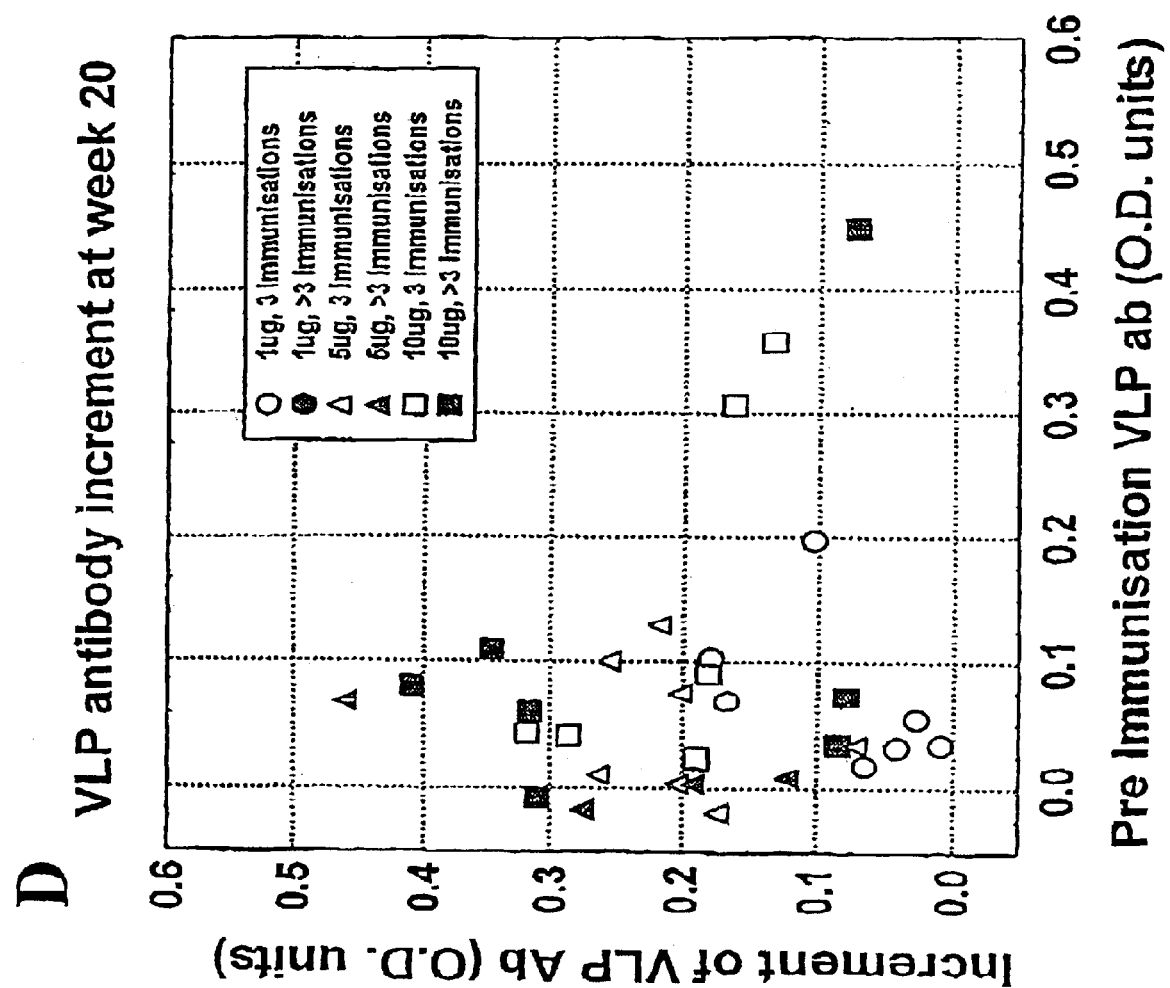
Figure 2E:
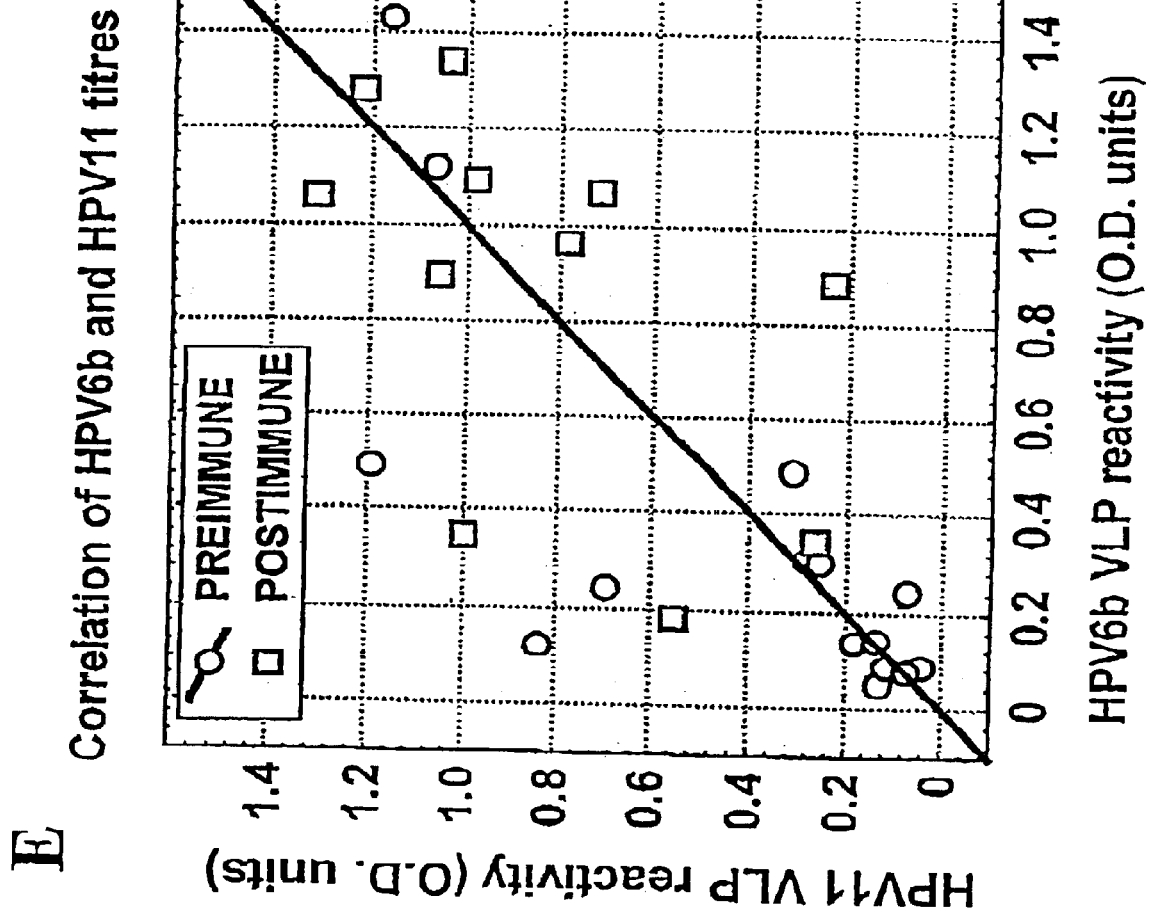

Prior to immunization, significant sero-reactivity to HPV6b, defined as OD reactivity >3 S.D. from the mean of pooled "normal" sera, was observed in 9 of 32 study subjects and reactivity to HPV16 was observed in two subjects (FIGS. 2A and 2B). In contrast, sero-reactivity to HPV6b was measurable in 0 of 38 control subjects and antibody to HPV16 VLPs in two of 38 control subjects. There was an increase in reactivity to HPV6b after immunization in all but one of the study subjects (FIG. 2D): the mean increase was 0.190 OD units +/- S.D. 0.110. The increase in VLP specific reactivity with HPV6bL1 VLPs at week 20 was greater for subjects receiving the 5 μg (0.227+/-0.028) and 10 μg (0.220+/-0.035) doses of VLPs than for those receiving the 1 μg (0.085+/-0.022) dose, and was non-significantly greater in those subjects who received 5 or 10 μg who received more than three immunizations (0.242+/-0.042, n=1 1) than in those who received three (0.209+/-0.021, n=13). Two weeks after the first VLP immunization, the largest increments in HPV6bL1 VLP specific IgG antibody titre were observed in those subjects with initially weakly HPV6bL1 reactive sera, suggesting that these subjects were already primed to HPV6b (FIG. 2C). Final levels of IgG antibody to HPV6bL1 VLPs were predicted by initial levels of VLP specific antibody ($r^2$=0.53; p=0.005), however, the increment in VLP reactivity observed following three immunizations did not correlate significantly with the initial VLP reactivity (FIG. 2C). Sera were tested for reactivity with VLPs of other HPV types. No increase was seen in HPV16L1 VLP reactivity following immunization in 32 sera (mean increase 0.009 +/-S.D. 0.043). Of 11 subjects tested for reactivity to HPV11 L1 VLPs who were initially reactive to HPV6b, or who acquired reactivity to HPV6b following immunization, 10 acquired reactivity of similar magnitude to HPV11 VLPs ($r^2$=0.75) (FIG. 2E).

Clinical Outcome

One purpose of this study was to establish whether the use of prophylactic VLP based vaccines would adversely affect the course of existing HPV infection. The complete regression rate for visible wart disease in this study over 20 weeks (FIG. 3A) was 25 of 33 evaluable patients (76%) or 25 of 36 subjects (69%) if outcome data were analyzed on an intention to treat basis. Of the eight evaluable subjects with residual disease at 20 weeks, five had substantial partial regression (>50% wart clearance). Over further follow up to nine months, no subject with complete clearance had recurrence of disease, and two further subjects had complete regression, one following destructive treatment and one spontaneously. Regression of warts amongst evaluable subjects receiving the 5 and 10 μg dose of vaccine was similar (FIG. 3B), whereas regression amongst the patients who received 1 μg occurred earlier after immunization.

The number of warts at entry to the study ranged from 1 to 15, and resolution of warts during the period of observation was more common amongst those with fewer warts (Table 2). Subjects resolving warts during the study had a mean of 3.8 warts at entry whereas non-resolvers had a mean of 6.8 warts (ANOVA: F=6.07 for wart number as a predictor of resolution. 1 d.f; p=0.019). Wart area at entry ranged from 25 to 950 mm$^2$. Mean wart area at entry amongst those subjects not clearing their warts during the study was 520 mm +/-120, whereas mean area amongst those clearing their warts was 260 mm +/-47 mm. (F=5.84; d.f.=1; p=0.02). Multivariate analysis indicated that differences in wart number and size between the different dosage groups (Table 1) could account for the clearance rate differences observed between the groups. Number of warts at entry was not a predictor of time to regression, or of initial VLP specific antibody titre. The reported duration of warts prior to commencement of immunotherapy ranged from 1 to 20 months, with a median value of two months. Prior duration of wart disease was not a predictor of outcome of disease (F=0.32; 1 d.f, p=0.57), of time to regression, or of initial VLP specific antibody titre (F=0.89; 4 d.f.; p=0.47). Of 33 subjects, 15 had had prior destructive treatment with diathermy. Prior treatment did not predict outcome, time to regression, or antibody titre at entry to the study. Age of patients ranged from 18 to 56 (mean 33) with 27 females and six males and neither age or sex significantly predicted regression of warts or time to regression (Table 3).

Correlation of Immunity with Outcome

Correlations were sought between wart regression and the response to the VLP immunization. There was no correlation between the level or presence of pre-existing VLP specific antibody, or of the magnitude of the DTH reaction, and the eventual outcome of the warts, or the time to regression (Table 3). The size of the antibody increment following immunization was negatively correlated with outcome. This may reflect the trial design, in that subjects who failed to resolve their warts were further immunized, although the number of doses of vaccine received did not predict the magnitude of the antibody increment observed.

Conclusions

Figure 3A:
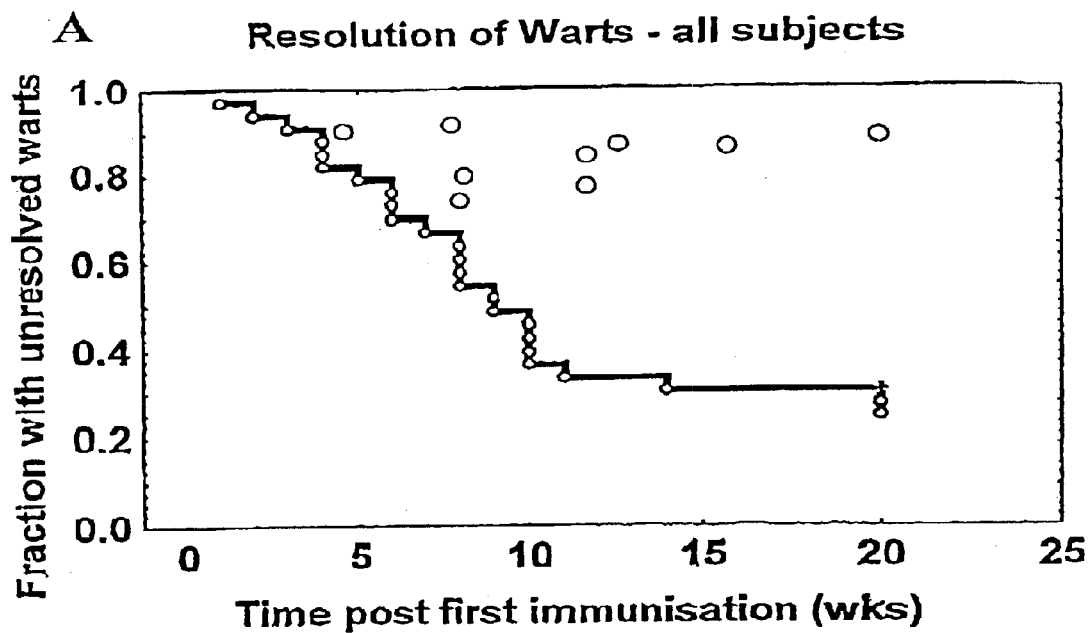
Figure 3B:
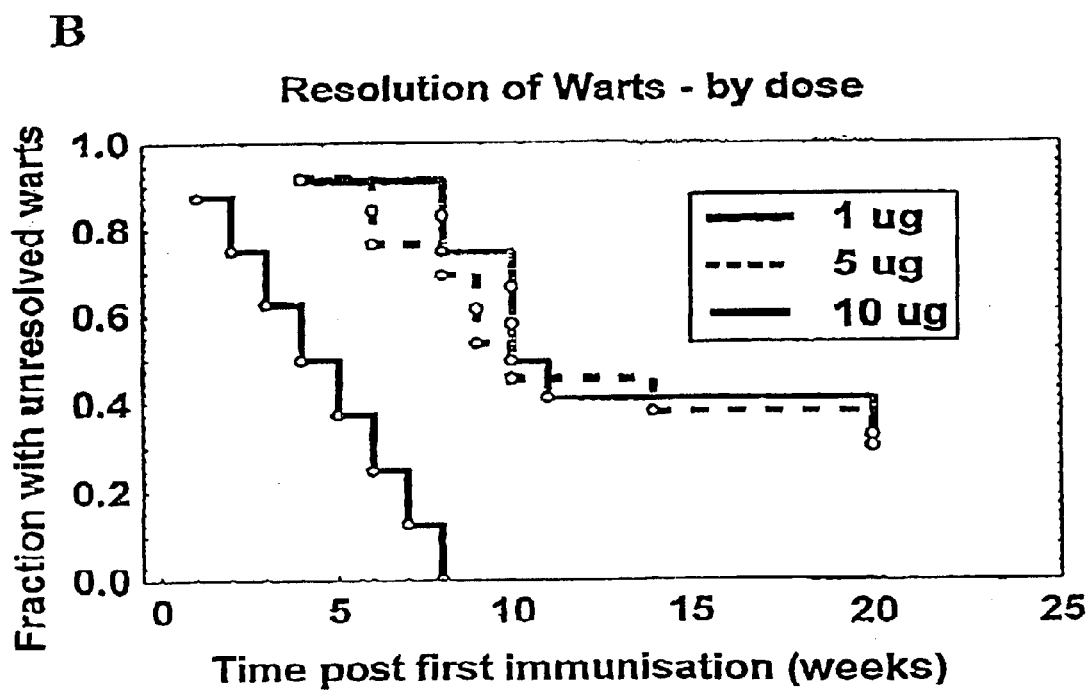

Regression of HPV6b+ve genital warts was observed over 20 weeks in the current study in 76% of HPV6b VLP immunized subjects. In contrast, the regression rate of genital warts over the same period in the control groups of published trials of therapy for genital warts range from 0–29% (FIG. 3A). Thus, not only has HPV6bL1 VLP administration not adversely affected the natural process of resolution of HPV6b associated warts but there is good evidence that the treatment may have accelerated resolution. A cellular inflammatory infiltrate, and in particular the presence of IL-12 secreting T cells as described in Coleman et al., 1994, Am. J. Clin. Pathol. 102 768–774, is associated with the process of resolution of genital warts: and an absence of cell mediated immunity is associated with failure of regression. These observations suggest a key role for cellular immunity in wart regression, as for other viral infections. PV viral capsid proteins including L1 are expressed in warts. Although detectable L1 protein is limited to the more superficial layers of the epidermis in warts, possibly as a consequence of L1 mRNA instability as described in Sokolowski et al, 1998, J. Virol. 72 1504–1515, cells expressing undetectably small amounts of L1 are nevertheless susceptible to L1 specific T cell mediated lysis as described in De Bruijn et al., 1998, Virology 250 371–376. Thus, even the minor amounts of L1 are expressed in the cells of the deeper layers of a wart may be sufficient to sensitize the replicating HPV infected parabasal keratinocytes in a wart to T cell mediated lysis. As administration of VLPs without adjuvant to animals induces VLP specific cytotoxic T cells as described in Peng et al., 1998, supra and Greenstone et al., 1998, supra, VLP immunotherapy may alter the outcome of human genital warts by induction of PV protein specific CTL which lyse the replicating HPV infected parabasal keratinocytes which allow wart persistence.

Passive specific immunotherapy of CMV and EBV infection with virus specific cytotoxic T lymphocytes (CTL) is effective immunotherapy in immunosuppressed subjects incapable of mounting an effective natural immune response to these viruses as shown in Sing et al., 1997, Blood 89 1978–1986 and Walter et al., 1995, N. Engl. J. Med. 333 1038–1044, confirming a role for CTL as immune effectors for reduction of infection in man. Immunization to induce cell mediated immunity has been proposed as active specific immunotherapy for herpes simplex viruses, and human immunodeficiency virus, but Phase 1 trials have to date failed to demonstrate clinical benefit, which as been attributed to the nature of the immune response induced by current immunization regimens. Naturally occurring papillomavirus infection is poorly immunogenic, presumably because the virus causes cell proliferation without local immunization, and infects only the superficial layer of the skin as shown in Frazer, I. H., 1996, Curr. Opin. Immunol. 8 484–491. Thus, specific immunotherapy for PV infection with VLPs in man might be expected to give a better clinical outcome than the immune response induced by infection, as is apparently demonstrated in the current study. Papillomavirus infection should therefore be a good candidate for studies of efficacy of newer vaccine delivery systems designed to produce effective cell mediated immunotherapy in man.

In addition to a role in immunotherapy of warts, induction of cell mediated immunity to HPV proteins would be a desirable feature in an HPV prophylactic vaccine, to eliminate any cells infected with HPV that escaped neutralization by VLP specific antibody. Demonstration of DTH to VLPs in subjects with genital warts in the present study is in keeping with the ability of VLPs administered without adjuvant to mice to induce cell mediated immune responses including specific CTL as described in Greenstone et al., 1998, supra, Peng et al., 1998, supra and Dupuy et al., 1997, Microb. Pathog. 22 219–225. It is yet to be determined whether the use of adjuvants which selectively stimulate cellular immunity will further enhance the efficacy of this therapeutic vaccine. As DTH testing might itself have induced immunity and administration of VLPs induces no local reaction in the ears of non-immune mice (data not shown), pre-immunization DTH testing was not carried out in this study, precluding a conclusion that HPV6bL1 specific DTH was a consequence of immunization. However, only a minority of subjects had pre-existing antibody to HPV VLPs, in keeping with the median lag time of six months demonstrated between acquisition of HPV16 infection and the appearance of HPV16 specific antibody in cohort studies as described in Carter et al., 1996, J. infect. Dis. 174 927–936. Thus, it is probable that the DTH reactivity in the current study was generally acquired as a result of immunization.

A significant increase in VLP specific antibody titre was observed in the current study in the majority of non-immune subjects after three immunizations and in partially immune subjects after one immunization. Thus, administration of VLPs to patients with HPV infection apparently induces immunity to the same epitopes as are immunogenic in the course of natural infection. Even 1 µg or less of VLPs are highly immunogenic in mice, rabbits, dogs and cattle, whether given with or without adjuvant as described in Breitburd et al., 1995, supra, Kirnbauer et al., 1996, supra and Christensen et al., 1994, J. Virol. 70 960–965. Murine Langerhans cells (LC) can express $\alpha 6\beta 1$ integrin as described in Price et al., 1997, J. Exp. Med. 186 1725–1735, recently described as a candidate receptor molecule for papillomavirus as described in Evander et al., 1997, J. Virol. 71 2449–2456, suggesting that direct uptake of PV VLPs by LC may explain their unadjuvanted immunogenicity. Administration of HPV6b VLPs produced humoral immune responses cross reactive with HPV11, but not with HPV16, confirming that VLP immunization induces antibody with cross reactivity between closely related PV types and a lack of cross reactivity between more distant types, as has been described following natural infection as described in Bernard et al., 1994, Curr. Top. Microbiol. Immunol. 186 33–54, Christensen et al., 1994, Virology 205 329–355 and Rose et al., 1994, J. Gen. Virol. 75 2445–2449 and Christensen et al., 1994, Virology 205 329–355. This observation is of significance for papillomavirus prophylactic vaccines.

The current data support the concept that HPVL1 VLPs are a good candidate for therapeutic vaccines against HPV infection.

In another embodiment of the invention there is provided a method of treatment of an existing PV infection which includes the step of administration of PV VLPs to a patient suffering from the PV infection. Such VLPs may include chimeric VLPs which comprise a protein E component.

In a further embodiment there may be provided a method of treatment of an existing PV infection which includes the step of administration of PV VLPs in the presence of adjuvant to a patient suffering from the PV infection. In this particular embodiment the adjuvant is preferably one that induces cellular responses and may be included from the group consisting of (1) lipid A and derivatives, (2) Quillaia saponins and derivatives, (3) mycobacteria and components or derivatives therefrom (4) IL 12, GMCSF and other Th1 inducing cytokines and (5) oxidized mannan and analogues therof.

TABLE 3

Predictors of wart resolution during the period of observation

|  | Resolved (n = 25) | Not resolved (n = 8) | P |
|---|---|---|---|
| Age | 33.4 ± 2.2 | 29.9 ± 3.2 | NS |
| Duration of warts (months) | 2.5 ± 0.8 | 1.8 ± 0.4 | NS |
| No. of warts at entry | 3.8 ± 0.5 | 6.8 ± 1.5 | P = 0.019 |
| Wart area at entry (mm$^2$) | 252 ± 48 | 520 ± 120 | P = 0.021 |
| DTH reaction to VLPs[A] | 2.32 ± 0.16 | 2.0 ± 0.37 | NS |
| VLP antibody pre-immunization[B] | 0.084 ± 0.021 | 0.080 ± 0.042 | NS |
| VLP antibody post immunization | 0.253 ± 0.026 | 0.347 ± 0.063 | NS |

TABLE 1

Study patient characteristics

| ID | Age/Sex | No. of warts | Site | Time mths | Area Mm$^2$ | Prv. Rx No | Dose (µg) | No. of doses | Resn (wk) | DTH | DTH Histo | VLP Ab Pre | VLP Ab Post |
|---|---|---|---|---|---|---|---|---|---|---|---|---|---|
| ZLY | 22F | 4 | vulva | 1 | 60 | 0 | 1 | 3 | 6 | 3 | 4 | .103 | .283 |
| LPP | 41F | 2 | vulva | 3 | 100 | 2 | 1 | 3 | 4 | 3 | 2 | .018 | .083 |
| LLL | 34F | 2 | multi | 1 | 125 | 0 | 1 | 3 | 2 | 1 | 2 | .054 | .082 |
| YXR | 50F | 2 | vulva | — | 200 | 0 | 1 | 3 | 1 | 3 | 2 | .034 | .043 |
| WY | 24F | 3 | cervix | 5 | 240 | 3 | 1 | 3 | 3 | 3 | 4 | .197 | .301 |
| XAQ | 32F | 4 | multi | 2 | 475 | 2 | 1 | 3 | 5 | 3 | 5 | .032 | .074 |
| FPY | 36F | 5 | vulva | 3 | 500 | 2 | 1 | 3 | 7 | 3 | 4 | .041 | .128 |
| QLH | 18F | 8 | vulva | 3 | 600 | 3 | 1 | 3 | 8 | 3 | 2 | .068 | .235 |
| RYL | 41F | 1 | vulva | 20 | 50 | 0 | 5 | 3 | 4 | 3 | 4 | .033 | .104 |
| ZJH | 27M | 2 | penis | 1 | 50 | 0 | 5 | 3 | 10 | 2 | 4 | .003 | .206 |
| ZCY | 24F | 1 | anus | — | 125 | 1 | 5 | 3 | 9 | 2 | Nd | .105 | .404 |
| SYF | 27F | 2 | vulva | 1 | 130 | 0 | 5 | 3 | 9 | 2 | 3 | .131 | .348 |
| PML | 43F | 3 | multi | 1 | 165 | 2 | 5 | 3 | 8 | 3 | 4 | .075 | .276 |
| JHF | 20F | 5 | multi | 2 | 240 | 2 | 5 | 3 | 20+ | nd | Nd | −.018 | .156 |
| XJF | 23F | 5 | vulva | 1 | 500 | 0 | 5 | 3 | 6 | 1 | 4 | .010 | .274 |
| LCL | 35F | 12 | multi | 1 | 750 | 0 | 5 | 3 | 6 | 2 | 4 | .100 | .355 |
| JHL | 32M | 2 | penis | 1 | 25 | 0 | 5 | 4 | 14 | 1 | Nd | .009 | .131 |

TABLE 2

Summary subject demographics, treatment regimes and outcome by immunization dose

| Group (Dose) | Number (F:M) | Age (years: mean, range) | No. of warts at presentation (Mean, range) | Area of warts at presentation (mm$^2$: mean, range) | Duration of warts (Months: mean, range) | Past Cautery (Yes:No) | Outcome at week 20 (resolved: persistant) | Mean time to resolution (Weeks: mean, range) |
|---|---|---|---|---|---|---|---|---|
| All subjects | 27F:6M | 32 (18–56) | 4.5 (1–14) | 325 (25–950) | 2.4 (1–20) | 15:18 | 25:8 | 11.0 (1–NR) |
| 1 µg | 7F:1M | 31 (18–50) | 3.8 (2–8) | 287 (60–600) | 2.6 (1–5) | 5:3 | 8:0 | 4.5 (1–8) |
| 5 µg | 10F:3M | 32 (20–50) | 4.3 (1–12) | 368 (25–900) | 2.8 (1–20) | 4:9 | 9:4 | 12.7 (4–N.R.) |
| 10 µg | 10F:2M | 33 (20–56) | 5.2 (1–14) | 282 (40–950) | 1.6 (1–3) | 6:6 | 8:4 | 13.4 (4–N.R.) |

LEGENDS

TABLE 3

[A] scored from 0 to 3 as described in Methods Section

[B] OD units for serum at 1:100 dilution tested against HPV6b VLPs in ELISA

FIG. 1

Immunohistochemical analysis of biopsy material from DTH reaction to HPV VLPs, collected from an immunized subject three weeks after the last dose of VLP vaccine and 48 hours after intradermal injection of 10 μg HPV6b VLPs.

Upper panel: CD3+ve T cells (brown) and CD8+ve T cells (red)

Lower panel: CD3+ve cells (brown) and DR+ve cells (red).

FIG. 2

Antibody to HPV6b (A) and HPV16L1 (B) capsid protein was measured at a serum dilution of 1:100 by ELISA assay using VLPs prepared with recombinant baculovirus. Results from subjects immediately prior to immunization [hatched] and at week 20 [solid], are shown.

- (C) Increase in HPV6b VLP specific IgG reactivity at week two of subjects immunized with HPV6b VLPs is plotted as a function of the initial HPV6bL1 VLP specific reactivity. The different symbols indicate the administered dose of VLPs.
- (D) Increase in HPV6b VLP specific reactivity at week 20 of subjects immunized with HPV6b VLPs is plotted as a function of the initial HPV6bL1 VLP specific reactivity. Open symbols are for subjects who received precisely three immunizations and closed symbols for those who received more than three immunizations. The different symbols indicate the administered dose per immunization.
- (E) Correlation of the reactivity of various sera with HPV6b and HPV11. Sera from prior to immunization are shown as circles and from week 20 as squares.

FIG. 3

Kaplan Meier analysis of time to wart clearance for subjects immunized with HPV VLPs.

- (A) All study participants.
- (B) Study participants stratified by dose of vaccine administered.

What is claimed is:

1. A method of treatment of an existing human papillomavirus (HPV) infection comprising: administering a therapeutic vaccine inducing cellular response comprising HPV VLPs selected from the group consisting of HPV L1 VLPs and HPV L1/L2 VLPs to a patient suffering from the HPV infection characterized in that said therapeutic vaccine excludes HPV E protein.

2. The method of treatment according to claim 1, wherein the HPV infection is characterized by the presence of epithelial lesions.

3. The method of treatment according to claim 2, wherein the epithelial lesions are selected from the group consisting of palmar warts, planter warts, anogenital warts, flat and planar warts of the skin and mucosal surfaces, CIN, and replicating or vegetative PV infection.

4. The method of treatment according to claim 3, wherein the epithelial lesions are genital warts caused by HPV 6, 11, 34, 39, 41, 42, 43, 44, 51, 52, 53, 54 or 55.

5. The method of treatment according to claim 4, wherein the genital warts are caused by HPV 6 and HPV 11.

6. The method according to claim 1, wherein the dosage of HPV VLPs administered to the patient is 0.5–20 μg.

7. The method according to claim 6, wherein the dosage is 1–10 μg.

8. The method according to claim 1, wherein HPV VLPs are administered 3–6 times over a period of 8–16 weeks.

9. The method according to claim 1, wherein HPV VLPs are administered 3–6 times over a period of 2–4 weeks.

10. The method according to claim 1, wherein the vaccine excludes adjuvant.

11. The method of treatment as claimed in claim 1, wherein the VLPs are produced by cloning the HPV L1 gene into a suitable vector and expressing L1 in an eukaryotic cell transformed by the vector.

* * * * *